United States Patent [19]

McConnell

[11] 4,222,744
[45] Sep. 16, 1980

[54] ASSAY FOR LIGANDS

[75] Inventor: Harden M. McConnell, Stanford, Calif.

[73] Assignee: Becton Dickinson & Company, Paramas, N.J.

[21] Appl. No.: 946,065

[22] Filed: Sep. 27, 1978

[51] Int. Cl.$^2$ .......................................... G01N 33/16
[52] U.S. Cl. ............................. 23/230 B; 23/915; 356/318; 356/417; 424/8; 424/12
[58] Field of Search ............... 23/230 D, 915; 424/12, 424/8; 356/318, 417

[56] References Cited

U.S. PATENT DOCUMENTS

| | | | |
|---|---|---|---|
| 3,939,350 | 2/1976 | Kronick | 424/8 X |
| 3,966,897 | 6/1976 | Renn | 424/8 X |
| 3,984,533 | 10/1976 | Uzgiris | 424/12 |
| 3,990,851 | 11/1976 | Gross | 23/230 B X |
| 4,011,044 | 3/1977 | Uzgiris | 23/230 B |
| 4,018,530 | 4/1977 | Hirschfeld | 356/317 X |
| 4,036,946 | 7/1977 | Kleinerman | 424/8 |
| 4,058,732 | 11/1977 | Wieder | 23/230 B UX |
| 4,100,416 | 7/1978 | Hirschfeld | 356/318 X |
| 4,102,990 | 7/1978 | Uzgiris | 424/8 X |
| 4,108,972 | 8/1978 | Dreyer | 424/8 X |

OTHER PUBLICATIONS

G. J. Buffone et al., Clin. Chem., 21 (12), 1731-1734 (1975).
G. Ertingshausen et al., Clin. Chem., 21 (9), 1305-1313 (1975).
D. Axelrod et al., Biophysical Jour., 16, 1055-1069 (1976).
D. E. Koppel et al., Biophysical Jour., 16, 1315-1328 (1976).
P. F. Fahey et al., Science, 195, 305-306 (Jan. 21, 1977).
J. Schlessinger et al., Science, 195, 307-309 (Jan. 21, 1977).

*Primary Examiner*—Sidney Marantz
*Attorney, Agent, or Firm*—Louis E. Marn; Elliot M. Olstein

[57] ABSTRACT

Assay for a ligand wherein the ligand is contacted in a fluid with (1) labeled binder or (2) binder and labeled reference ligand, and the presence of ligand determined from the movement of labeled material in at least one region of the fluid. In a particular assay, the label is a fluorescent material and ligand is determined from a change in fluoresence-time relationship in a region of the fluid.

56 Claims, 6 Drawing Figures

ASSAY FOR LIGANDS

This invention relates to the assay of ligands, and more particularly to an assay for ligands employing the use of a fluorescent material.

In general, ligands are assayed by a radioassay procedure which involves competition between the ligand and a radio-labeled form thereof for a limited number of binder sites. Thus, for example, when a known quantity of a labeled form of the ligand, a known quantity of a binder for the ligand and a sample containing the ligand are combined and incubated, the percentage of the radio-labeled form of the ligand bound to the binder will vary inversely with the quantity of ligand in the sample. After separating the ligand and radio-labeled ligand bound to the binder from the ligand and radio-labeled ligand not bound to the binder, the amount of radio-labeled ligand in either the bound or free fractions or both may be compared with a standard curve to determine the quantity of ligand which was present in the sample.

Such assays require the use of radioactive materials which has obvious disadvantages; such as, waste disposal, storage of the materials, the use of an expensive counter and the like. In addition, such assays require the separation of the bound and free portions, and are also generally time consuming.

As a result, there is a need for improved assays for ligands.

In brief, the present invention provides an assay for a ligand by contacting in a fluid a sample containing or suspected of containing the ligand with (1) a binder for the ligand which is labeled with a detectable substance or (2) a binder for the ligand and a reference ligand which is labeled with a detectable substance, and determining the movement of the labeled material in a region of the fluid to determine the presence of ligand in the sample. The movement of labeled material in the region can be determined by measuring the relationship of the change in the amount of labeled material in the region and time; i.e., the time to achieve certain changes in amounts and/or the changes in amounts achieved after certain time. The assay is based on the principle that the movement of components in the fluid (binder and/or ligand and/or reference ligand) are changed by binding of ligand and/or reference ligand to the binder; i.e., (1) the bound product of ligand and binder moves in the fluid at a rate measurably different from the unbound binder; or (2) the unbound reference ligand moves in the fluid at a rate measurably different from the bound product of reference ligand and binder; or (3) the bound product of reference ligand and binder moves in the fluid at a rate measurably different from the bound product of ligand and binder.

The fluid in which the assay is effected is preferably a liquid; however, it is to be understood that the fluid could also be a solid; e.g., a gel. Thus, the term "fluid" as used herein refers to a material in which at least one labeled component in the assay mixture is capable of movement.

The movement of the ligand, binder and reference ligand in the fluid results from diffusion in the presence and/or absence of an applied force. Thus, in the absence of an applied force, the movement of the ligand, binder and reference ligand results from thermal diffusion. Such movement by thermal diffusion can be supplemented by application of a force such as one or more of an electrical force, magnetic force or gravitational force. The use of such expedients will be hereinafter described in more detail.

In accordance with one aspect of the present invention, in the case where the unbound binder moves in a fluid at a rate which is measurably different from the binder bound to the ligand, a sample containing or suspected of containing the ligand is added to a fluid containing a binder therefor, which is labeled with a detectable substance. Any ligand present in the sample will bind to the binder which will change the rate of movement of total labeled binder in the fluid as a result of the difference in the rate of movement between the unbound binder and the binder bound to the ligand. The presence of ligand in the sample can be determined either qualitatively or quantitatively by determining the movement of the labeled material; i.e., labeled binder (bound and unbound) in a region of the fluid. Such movement can be measured by measuring a change in the amount of labeled material in the region with respect to time.

In accordance with another aspect of the present invention, in the case where an unbound reference ligand moves in a fluid at a rate which is measurably different from the reference ligand bound to a binder, a sample containing or suspected of containing the ligand is contacted, in a fluid, with binder and reference ligand which is labeled with a detectable substance. The presence of ligand in the sample effects the relative amount of bound and unbound reference ligand, which in turn effects the rate of movement of total labeled reference ligand (bound and unbound) as a result of the difference in movement between unbound labeled reference ligand and labeled reference ligand bound to the binder. The presence of ligand in the sample can be determined either qualitatively or quantitatively by determining the movement of labeled material; i.e., labeled reference ligand (bound and unbound) in a region of the fluid. Such movement can be measured by measuring a change in the amount of labeled material in a region of the fluid with respect to time.

In accordance with a further aspect of the present invention, in the case where a reference ligand bound to a binder moves in a fluid at a rate which is measurably different from the ligand bound to the binder, a sample containing or suspected of containing the ligand is contacted, in a fluid, with binder labeled with a detectable substance and reference ligand which is a form of the ligand modified in a manner such that the bound product of binder and reference ligand moves in the fluid at a rate which is different from the bound product of binder and ligand. Such modification of the reference ligand can be accomplished, for example, by supporting the reference ligand on a solid support. The presence of ligand in the sample affects the relative amount of bound and unbound reference ligand in the fluid, which in turn affects the rate of movement of total labeled binder (bound to the reference ligand and bound to the ligand) in the fluid as a result of the measurable difference in movement between the labeled binder bound to the ligand and the labeled binder bound to the reference ligand. The presence of ligand in the sample can be determined either qualitatively or quantitively by determining the movement of the labeled material; i.e., labeled binder (bound to the ligand and and bound to the reference ligand) in a region of the fluid. Such movement can be measured by measuring a change in the amount of labeled material in a region of the fluid with respect to time.

The present invention is applicable to assays for a wide variety of ligands for which an appropriate binder can be found, such as (1) antigens, which when introduced into the blood stream of a vertebrate result in the formation of antibodies; (2) haptens, which when bound to an antigenic carrier and introduced into the blood stream of a vertebrate, produce antibodies specific for the hapten or (3) ligands which have naturally occurring binders which can be isolated in a form specific for the ligand, such as, for example, serum proteins; binders extracted from various animal organs; serums; milk binders, binders of bacterial origin such as staphylococcus aureus, which is a binder for IgG; and the like. It is also to be understood that the ligand could be an antibody or a naturally occurring binder, in which case the binder for the ligand would be an antigen or an antibody to such antibody or naturally occurring binder.

As representative examples of ligands which can be assayed in accordance with the present invention, there may be mentioned:

(1) drugs, including alkaloids; e.g., such as morphine, heroin and the like; methandone and its analogs; megerdine and its analogs; indole alkaloids; catecholamines; barbiturates; glutethimide; cocaine and its metabolites and analogs; dyphenyl hydantoin, marijuana; tranquilizers, e.g., meprobamate; benzoliazocycloheptanes; phenothiazines, etc.;

(2) amino acids, polypeptides, nucleotides, nucleosides and proteins, such as ACTH, oxytocin, lutenizing hormone, insulin, Bence-Jones protein, chorionic gonadotropin, pituitary gonadotripin, growth hormone, renin, thyroxine binding globulin, bradykinin, angiotensin, follicle stimulating hormone; cyclic AMP, cholyl glycine, cyclic GMP, etc;

(3) steriods, including; oestrogens, gestrogens, androgens, adrenocortical hormones, bile acids, cardiotonic glycosides, aglycones as well as saponins. As specific examples, these may be mentioned; testosterone, androsterone, equilenin, estone, estriol, progesterone, pregnenolone, 17-hydroxydioxy-corticosterone (compound S), dexoycorticoserone, cortisone, corticosterone, cortisol, aldosterone, digoxin, digitoxin, etc.;

(4) vitamins, such as vitamin A, the B vitamin group, vitamin C, the D vitamins, and vitamins E and K; and miscellaneous biological substances, such as, antibodies, e.g., penicillin, tetracycline, antigens for Viral Hepatitis A and B, Rubella, Herpes Simplex, Alphafeto protein, $T_3$, $T_4$, TSH, CEA, antibodies to N gonorrhea, Dane Cores, Viruses, virus derived proteins and nucleic acids and lipids.

The term "ligand", as used herein, encompasses antigens, haptens, materials which have naturally occurring binders, as well as antibodies and the naturally occurring binders.

The term "binder" is a substance which binds the ligand, and encompasses antigens, antibodies, naturally occurring binders and antibodies produced in response to antibodies; e.g. IgG anti IgG.

The term "reference ligand" refers to an encompasses a substance which is bound by the binder for the ligand. The reference ligand may be the ligand or appropriate analog thereof, which is labeled or unlabeled with a detectable substance or which is modified to move at a rate different than the ligand. As a result, the reference ligand can be an antibody, antigen, hapten or material having a naturally occurring binder.

In effecting the assay, the binder and/or reference ligand may be labeled with a detectable substance.

The reference ligand and/or binder are labeled with a detectable substance, with the detectable substance preferably being an optically detectable substance, and most preferably a substance which fluoresces. The substance employed as a label should be one which does not interfere with the immunochemical reaction; i.e., minimal cross reactivity and/or blocking of binding. In the case of employing a fluorescent substance, wherein the assay employs photobleaching, as hereinafter described, the fluorescent material should be one which is photobleachable, preferably one which is photobleachable at low power levels. The selection of a suitable material for labeling is deemed to be within the scope of those skilled in the art from the teachings herein. As representative examples of suitable fluorescent materials, there may be mentioned; fluorescein, aminofluorescein, rhodamine, D.A.N.S. (1-dimethyl amino-naphthalene-5-sulfonic acid) ethiduim bromide, N.B.D. chloride, rosamine, acridine orange, laser dyes, and the like.

The detectable substance, and in particular the fluorescent material, may be employed as the label by causing such material to become attached or bound to the binder and/or reference ligand. In many cases, the fluorescent material will bind directly to the binder or reference ligand, as known in the art. In other cases, the fluorescent material may be linked to the reference ligand or binder by the use of a suitable coupling agent, as known in the art. As representative examples of suitable coupling agents, there may be mentioned: dialdehydes, e.g., glutaraldehyde, succinaldehyde, malonaldehyde; etc., carbodimides; diisocyanates; dimethyl adipimate; isothiocyanate; cyanuric chloride; and the like. It is to be understood that the binder and/or reference ligand can be labeled with more than one fluorescent molecule by providing multiple sites; e.g., by attaching a polymeric chain which has a multiplicity of fluorescent molecules coupled thereto. Such procedures are described, for example, in U.S. Pat. No. 4,018,530 and the applications incorporated by reference thereto. As a further alternative, the multiplicity of fluorescent molecules can be provided by including a multiplicity of such fluorescent molecules in or on a solid material, such as beads, and linking the binder to such beads. This method is of particular use in the case where the binder is supported on a solid support for use in the assay, as hereinafter described in more detail.

A fluorescent material may be attached to a binder, such as for example, an antibody, by attaching the fluorescent material to an antibody to the antibody employed as a binder; for example, binding fluorescent labeled IgG anti IgG to IgG.

A convenient method of providing a fluorescent label for a binder and/or reference ligand is through a primary amino group of the binder and/or reference ligand which is then reacted with fluorescein derivatized with isothiocyanate. A substance having a terminal sugar group, such as digoxin, can be labeled with a fluorescent material by opening the terminal sugar group with periodate, followed by reaction with ethylenediamine. The resultant Schiff's base is reduced with borohydride and the resulting primary amine can then be reacted with isothiocyanate derivatized fluorescein.

The labeling of binder or reference ligand with a fluorescent material is deemed to be well within the scope of those skilled in the art from the teachings herein, and as a result, no further description in this respect is deemed necessary for a complete understanding of the present invention.

In accordance with a preferred aspect of the present invention, the assay is effected by determining the movement of fluorescent labeled material in a region of the fluid to determine the presence of ligand in a sample. The movement of fluorescent labeled material in the region can be determined by measuring the change in the amount of fluorescent labeled material in the region with respect to time. Such change in the amount of labeled material in the region with respect to time can be determined by measuring an increase and/or decrease in fluorescence in the region with respect to time.

Thus, for example, such movement could be determined by subjecting a region of the fluid to photobleaching radiation, followed by measuring the increase in fluorescence with respect to time, which is dependent upon the movement of additional fluorescent material into such region or portion thereof. Alternatively, a region of the fluid can be subjected to photobleaching radiation and measuring the decrease in fluorescence with respect to time during bleaching which is dependent upon movement of additional fluorescent material into the region; i.e., the fluorescence in the region decreases at a slower rate as the rate of movement of fluorescent material from outside the bleached region into the bleached region increases or by measuring the decrease in fluorescence in an adjacent region which is dependent upon the movement of bleached material into the adjacent region. As hereinabove described, such movement of fluorescent material results from diffusion in the presence or absence of an applied force.

In accordance with an aspect of the present invention wherein the rate of movement of a binder in a fluid can be measurably changed by binding of ligand thereto, an assay for a ligand can be effected by contacting the ligand, in a fluid, with the binder labeled with a fluorescent material. A region of the fluid is photobleached and the recovery of fluorescence in such region is measured with respect to time. Applicant has found that the recovery of fluorescence with respect to time in the region decreases as the amount of ligand in the fluid increases in that the bound product of ligand and binder labeled with fluorescent material moves at a rate which is slower than the rate of movement of the unbound binder labeled with the fluorescent material. Since the recovery of fluorescence in the region with respect to time is related to the amount of ligand in a sample, the presence of ligand in the sample can be determined quantitatively. Thus, in accordance with the present invention, a standard can be prepared by contacting various known amounts of a ligand and a fixed quantity of binder labeled with a fluorescent material (the fixed quantity is an excess of that required to bind all ligand) followed by photobleaching and measuring the recovery of fluorescence with respect to time for each of the various known amounts of ligand. An unknown quantity of ligand in the sample can then be determined by contacting in the fluid the sample which contains or is suspected of containing the ligand, and the fixed quantity of binder labeled with a fluorescent material followed by photobleaching and measuring the recovery of fluorescence-time relationship, i.e., the time to achieve a specific recovery of fluorescence or the recovery of fluorescence after a specific time. The amount of ligand present in the sample can then be determined by comparison with the previously determined values, i.e., the standard. Alternatively, as hereinabove described, the standard can be obtained by photobleaching and measuring the decrease of fluorescence in the region or adjacent region with respect to time. An unknown quantity of ligand in the sample can then be determined by measuring the decrease in fluorescence-time relationship, i.e., decrease in fluorescence after a specific period of time or the time required to obtain a specific decrease in fluorescence, and comparison with the previously determined values, i.e., the standard.

In accordance with an aspect of the invention wherein the rate of movement of a reference ligand in a fluid is measurably changed by binding of the reference ligand to a binder, a ligand can be assayed by contacting in a fluid a sample containing or suspected of containing the ligand, binder and reference ligand labeled with a fluorescent substance. A region of the fluid is photobleached, and the relationship between recovery of fluorescence in the region and time is determined. Applicant has found that the rate of recovery of fluorescence increases as the amount of ligand in the sample increases in that as the amount of ligand in the sample increases the amount of reference ligand labeled with a fluorescent substance bound to the binder decreases. In view of the fact that the reference ligand bound to the binder moves at a slower rate then unbound reference ligand, there is an increase in the rate of recovery of fluorescence in the region as the amount of ligand in the sample increases.

In accordance with the present invention, a standard is prepared by contacting various known amounts of a ligand with fixed quantities of binder and fixed quantities of reference ligand labeled with a fluorescent material, (the fixed quantity of reference ligand labeled with a fluorescent material is in excess of that which can be bound to the binder) followed by photobleaching and determining the recovery of fluorescence in the region-time relationship for each of the known amounts of ligand. An unknown quantity of ligand in the sample can then be determined by contacting in a fluid the sample containing or suspected of containing the ligand, the fixed quantity of binder and the fixed quantity of reference ligand labeled with the fluorescent material, followed by photobleaching, and determining the recovery of fluorescence in the region-time relationship. The amount of ligand present in the sample can be determined by comparing the recovery of fluorescence after a specific time or the time required to obtain a specific recovery of fluorescence with the previously determined values for the previously mentioned known quantities of ligand.

Alternatively, as hereinabove described, the standard can be obtained by photobleaching, and measuring the decrease in fluorescence-time relationship during such photobleaching for various known amounts of ligand. An unknown quantity of ligand in a sample can then be determined by measuring the decrease in fluorescence-time relationship for such sample and comparison with the previously obtained values; i.e., decrease in fluorescence after a specific time or time to obtain a specific decrease in fluorescence.

In accordance with aspect of the present invention wherein a binder bound to a reference ligand moves in a fluid at a rate which is measurably different from the binder bound to a ligand, an assay for a ligand can be effected by contacting in a fluid the ligand, binder labeled with a fluorescent substance, and a reference ligand which is modified to move in the fluid at a rate which is measurably different from the ligand, whereby the bound product of binder and reference ligand moves in the fluid at a rate which is different than the bound product of binder and ligand. The reference ligand can be modified to have such a different rate of movement in a wide variety of ways; for example, by placing the reference ligand on a suitable solid, such as a bead or the like. Alternatively, the reference ligand can be modified, in the case where movement is to be effected by the application of a force, such as an electric force, by providing the reference ligand with a charge whereby the reference ligand moves at a rate different from the ligand. In the case where movement is to be effected by the application of a magnetic force, the reference ligand can be attached to a suitable magnetic material to provide the reference ligand with a rate of movement in the magnetic force field which is different than the ligand. A region of the fluid is photobleached and the relationship of the recovery of fluorescence in the region with respect to time is determined. Applicant found that the recovery of fluorescence with respect to time, in the case where the reference ligand has been modified to move at a rate slower than the ligand, increases as the amount of ligand in the sample increases in that the amount of binder bound to the ligand, as compared to the amount of binder bound to the reference ligand increases with an increase in the amount of ligand present in the sample. In view of the fact that the binder labeled with a fluorescence substance when bound to the ligand moves at a faster rate than the binder labled with the fluorescent substance bound to the reference ligand, an increase in the amount of ligand in the sample results in an increase of recovery of fluorescence in the region with respect to time. In accordance with the present invention, a standard can be prepared by contacting various known amounts of a ligand with fixed quantities of binder labeled with a fluorescent material and fixed quantities of reference ligand, modified as hereinabove described, followed by photobleaching of a region of the fluid and determining the relationship between increase of fluorescence in the region and time for each of the known amounts of ligand. An unknown quantity of ligand in a sample can then be determined by contacting in a fluid the sample containing or suspected of containing the ligand, the fixed quantity of binder labeled with a fluorescent substance and the fixed quantity of modified reference ligand, followed by photobleaching and determining the recovery of fluorescence in the region as related to time. The recovery of fluorescence at a specific time or the time required to obtain a specific recovery of fluorescence is then compared with the values obtained for the aforementioned known quantities of ligand to determine the amount of ligand present in the sample. As hereinabove described, in the alternative, the standards can be prepared by photobleaching a region of the fluid and determining the relationship between decrease in fluorescence in the region with respect to time, with such decrease proceeding at a slower rate as the amount of ligand in the sample increases in that the rate of movement of fluorescent material into the region increases as the amount of ligand increases in that the bound product of fluorescent labeled binder and ligand moves at a faster rate than the bound product of fluorescent labeled binder and reference ligand.

As hereinabove indicated, the movement in the fluid can be effected by the application of an appropriate force field; for example, one or more of an electrical field, gravitational field, e.g. settling, centrifugation, or magnetic field. Thus, for example, by applying an electric field to the fluid, by the application of an A.C. or D.C. potential, the movement of the ligand, binder or reference ligand can be increased, depending upon the charge, ionic strength of the fluid, etc. Such an electrophoretic effect provides an additional means of discrimination for effecting the assay. Thus, the electrophoretic voltage can be used to enhance the assay accuracy. For example, in the absence of any voltage pulse, a single fluorescent labeled substance is characterised by essentially two quantities, the sensitivity to bleaching and the movement rate; in particular, the diffusion constant. In the presence of a voltage pulse, a fluorescent labeled substance can show a dependence on applied potential. Thus, movement of the substance in the fluid can be changed by changing the charge of the substance. For example, in a case where a ligand and a binder may have similar diffusion constants, a difference in the rate of movement between the ligand and binder can be provided by adjusting the charge on the binder whereby upon applying an appropriate voltage, the binder and ligand will have a different rate of movement in the fluid, notwithstanding similar diffusion constants. Similarly, the sensitivity of an assay can be increased by increasing the difference in the rate of movement between a labeled reference ligand and binder by the application of electrophoretic voltages. For example, both bleaching and recovery of fluorescence can be measured while applying electrophoretic voltages to provide for an appropriate difference in the rate of movement of binder and labeled reference ligand.

Alternatively, electrophoretic voltages could be applied only during bleaching to increase, for example, the discrimination between binder and labeled reference ligand. For example, by providing the binder with a net charge and the labeled reference ligand with no net charge, and applying an A.C. field during bleaching, the bound labeled reference ligand will be driven into and out of the bleaching region, whereas the unbound labeled reference ligand will not. As a result of the increased bleaching of bound labeled reference ligand its rate of recovery will be reduced during the recovery portion of the assay (which is effected without the A.C. field) and the discrimination between bound and unbound labeled reference ligand is increased. Alternatively, the A.C. field could be applied only during the recovery portion of the assay to increase the rate of recovery of bound labeled reference ligand which also increases the discrimination between bound and unbound labeled reference ligand.

The use of electrophoretic voltages may also be employed to avoid the problems of interfering substances which may be present in the fluid. This can be accomplished by adjustment of electrophoretic mobilities, as by changing pH, and voltage pulses, so as to discriminate against the interfering substances. The application of A.C. electrophoretic voltages can also be used to discriminate against such factors as fluorescent background or "noise" if the electrophoretic mobility of the background substance and/or the substance to be detected can be appropriately adjusted. Thus, for example, in an assay employing labeled reference ligand and binder, the binder can be provided with a net charge and the labeled reference ligand with no net charge. On the application of an A.C. field, the labeled reference ligand bound to the binder will move at a certain frequency and the assay can be effected by detecting only light emitted from fluorescent material moving at such frequency to thereby discriminate bound labeled reference ligand from unbound labeled reference ligand as well as interfering fluorescent substances if present.

In accordance with another aspect, a magnetic force field may be applied to affect the movement of the various substances employed in the assay. In using such a magnetic force field, one or more of the substances to be employed in the assay is attached to appropriate magnetic material; for example, in the form of magnetic particles or beads. For example, an assay could be effected with the fluorescent labeled binder supported on magnetic beads. The presence of ligand in the sample will effect cross linking of the beads, which will change the rate of movement of the fluorescent material in the magnetic field. Following the hereinabove described principles, wherein a region of the fluid is subjected to photobleaching, an increase in the amount of ligand in the sample will produce an increase in the cross linking of the fluorescent labeled binder coated magnetic beads, which will produce a corresponding change in the relationship of change of fluorescence and time. It is to be understood that the fluorescent label could be applied to the beads instead of the substance which is supported on such beads; however, this expedient still results in such substance being labeled with the fluorescent material, although through the bead intermediate. It is to be understood that a magnetic force field could be employed to increase the sensitivity of the assay by increasing the difference in the rate of movement between a labeled reference ligand and binder, in a manner similar to the use of electrophoretic voltages. Thus, for example, binder could be supported on a magnetic particle and a magnetic field applied during bleaching to increase the photobleaching of labeled reference ligand bound to the binder, with the magnetic field not being applied during the recovery portion of the assay to thereby decrease the rate of recovery of bound labeled reference ligand and thereby increase discrimination between unbound and bound labeled reference ligand. Alternatively, the magnetic field can be applied only during the recovery portion of the assay, as hereinabove described with respect to the application of an electric force field. The use of such a magnetic force field provides a further dimension in discriminating the movement of the various substances to be employed in the assay.

Movement can also be affected by a gravitational force field, such as by settling, or by the use of a centrifugal force. Thus, for example, one of the substances to be used in the assay can be supported on a solid support, such as beads, with the supported substance in the fluid being subjected to a gravitational force. In one such case, fluorescent labeled binder can be coated on appropriate beads, and the presence of ligand in a sample results in cross linking of the beads, which increases the rate of settling thereof. In an assay procedure, as hereinabove described, employing, for example, photobleaching, the assay can be effected in a vertically disposed sample container, with the photobleached region being in a lower portion of the container. As the amount of ligand increases in the sample, there is an increase in the cross linking of the fluorescent labeled binder coated beads, which increases the settling rate thereof, whereby there is an increase in the recovery of fluorescence in the photobleached region with respect to time. Thus, the use of a gravitational force field provides another dimension for varying the movement of the substances employed in the assay in the fluid.

It is also to be understood that the assay could be effected with one of the substances supported on a solid support, without applying a force field whereby movement is effected by thermal diffusion. Thus, for example, in the case where a binder and fluorescent labeled reference ligand have similar diffusion constants, the binder can be supported on a solid support, such as beads, to change the diffusion constant thereof, whereby the bound product of binder and labeled reference ligand are moved at a rate which is different than the unbound reference ligand labeled with fluorescent substance. Solid supports can also be employed to increase assay sensitivity by increasing the difference in the appropriate diffusion constants. For example, a binder can be supported on a solid support to further increase the difference between the diffusion constant of a binder and reference ligand. Alternatively, as hereinabove described, reference ligand can be supported on a solid support to change its diffusion constant with respect to ligand and the assay effected with labeled binder.

The use of solid materials, such as beads, may also be employed to increase the amount of fluorescent material employed to label a substance used in the assay. Thus, for example, in a case where binder is to be labeled with a fluorescent substance, a multiplicity of fluorescent molecules can be applied on or within a bead, and the binder supported on such bead, whereby the binder is provided with a plurality of fluorescent labeled molecules. The use of such a plurality of fluorescent labeled molecules can increase the sensitivity of the assay by decreasing the amount of binder which is to be used in the assay.

In employing the assays as hereinabove described, it is to be understood that although bleaching of a region is preferably effected by photobleaching, it is also possible to effect such bleaching other than by the use of a bleaching pulse of light. For example, such bleaching in such region could be effected electrically.

The present invention will be further described with respect to the following drawings, wherein.

The detecting system will be described with respect to a procedure by which movement is effected by thermal diffusion, and in which the assay is effected by use of a binder and a reference ligand labeled with a fluorescent material, which employs photobleaching. In brief, such an assay involves mixing of sample ligand, reference ligand labeled with a fluorescent substance, and binder, in solution, followed by irradiation for a time and with light intense enough to cause bleaching (irreversible photodecomposition) of the fluorescent labels in the irradiated region. This region is then monitored for fluorescence with a light beam in a manner such that there is no further or negligible bleaching. The monitoring or probing so as to produce no further or insignificant bleaching (hereinafter referred to as non-bleaching) may be effected with light of less intensity and/or light of a similar intensity for a shorter duration so as to produce non-bleaching. The fluorescence recovers (increases) with time due to thermal diffusion of fluorescent labels into the beam, in the form of fluorescent labeled reference ligand which is bound to the binder, and fluorescent labeled reference ligand which is unbound. The rate of fluorescence recovery is dependent on the ratio of unbound reference ligand to bound reference ligand, because the larger complex of the bound reference ligand diffuses more slowly than does the unbound reference ligand. Therefore, the standard curve of fluorescence recovery at a specific time or time for a specific fluorescent recovery versus sample ligand concentration can be constructed, from which concentration of unknown ligand samples can be determined.

Figure 1:
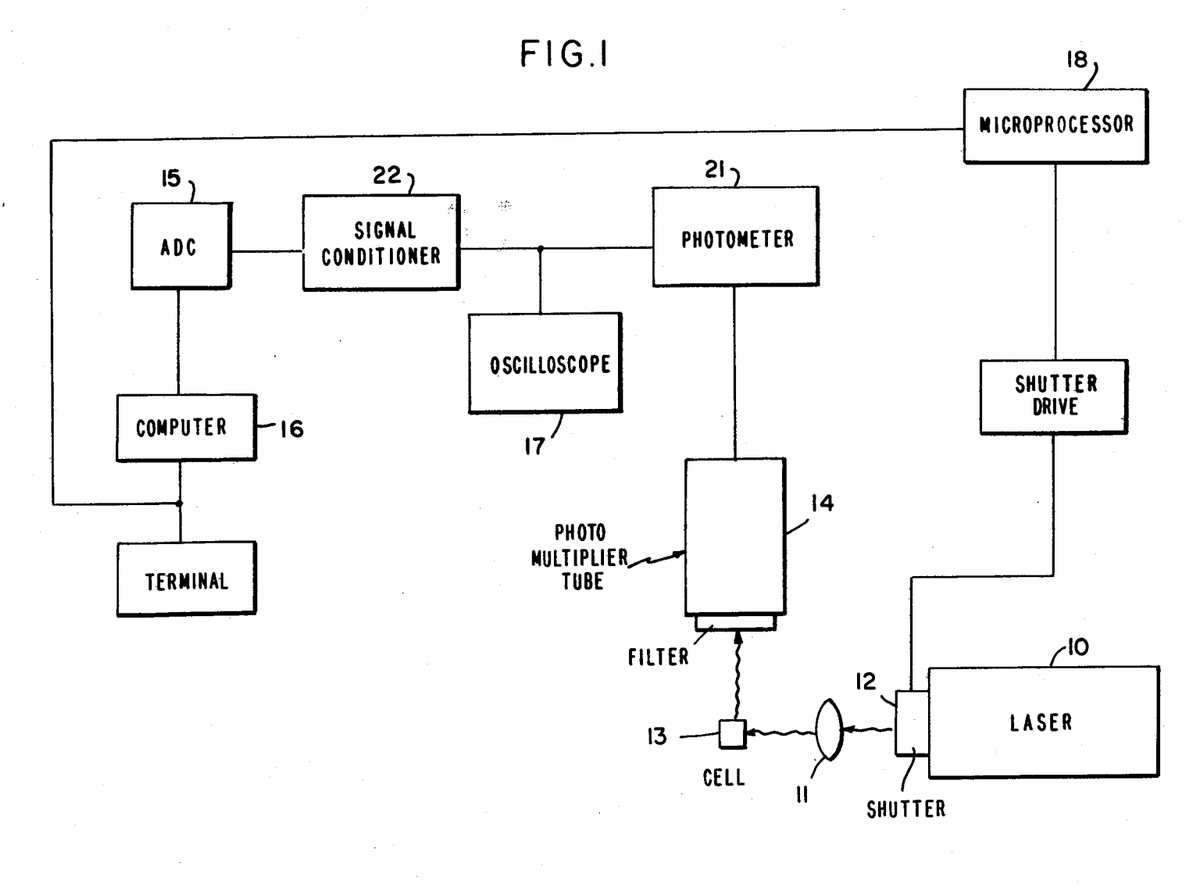
FIG. 1 is a simplified schematic diagram of a detecting system for effecting the assay of the present invention.

Referring now to FIG. 1, there is shown a radiation source such as a light source for exciting the wave length of fluorescent material employed in the assay so that such material fluoresces. The light source is particularly shown as a laser, such as an argon ion laser which produces a beam of light, with such laser being indicated as 10. Disposed in the path of the beam of light from light source 10 is an optical train 11, which may contain one or more lenses, for focusing light from source 10 which passes through shutter 12, onto a sample holder such as a cuvette, generally indicated at 13. The equipment is designed such that the light source illuminates only a limited region of a sample in the sample holder 13.

A photodetector, such as a photomultiplier tube 14 converts the amplitude of the light emitted from the excited fluorescent material in sample holder 13 into a proportional electrical signal, such as currents. The output of photomultiplier tube 14 is connected through a photometer 21 and signal conditioner 22 to an analogue to digital converter, schematically generally indicated at 15 for converting the currents to numbers, which are fed to a computer, schematically generally indicated as 16 to provide for a read out of such numbers, as required. The photomultiplier tube 14 may be also or alternatively connected to an output display system, such as a storage type cathode ray oscilloscope 17 for providing a visual read out. Both the analogue to digital converter 15 and the shutter 12 are operated through a microprocessor, schematically generally indicated as 18.

In operation, for example, a ligand, a reference ligand labeled with a fluorescent substance, and binder, in a fluid, are placed in sample holder 13. The microprocessor opens shutter 12 to provide a light pulse which is a non-bleaching light pulse (probe pulse) to measure the amount of fluorescent material in the irradiated region before bleaching. The converter 15 converts the current received from photomultiplier tube 14 to a number for the computer. A second light pulse, which is for a duration to effect photobleaching of fluorescent material in the test region is then initiated to reduce the light emission in such test area. It is not necessary to effect the photobleaching for a period of time in order to quench all light emission. The light beam is focused to be small and intense in order to effect the photobleaching in the test region and is preferably effected in a manner such that the bleach time is as short as possible in order to obtain essentially no diffusion during the bleaching. Subsequently, at predetermined time intervals, the shutter is opened for a predetermined duration, and the photomultiplier tube 14 detects the amount of light emitted from such region at such time, which is converted to a proportional electrical signal. The converter 15 converts such electrical pulses to numbers which are fed to computer 16. The computer can provide a read out of the recovery of fluorescence at any time t, as follows:

$$R_t = (P_t - P_3)/(P_1 - P_3)$$

wherein $R_t$ is fluorescent recovery at time t;

$P_t$ is a signal representing the quantity of light in the test region at time t;

$P_1$ is a signal representing the quantity of light in the test region immediately prior to photobleaching; and $P_3$ is a signal representing the quantity of light in the test region immediately after photobleaching.

As a result of thermal diffusion, increasing quantities of fluorescent material move into the test region, whereby each subsequent probe pulse over the length of the test results in an increasing amount of light being emitted to photomultiplier tube 14. In this manner, the photomultiplier tube 14 measures the relationship between the recovery of fluorescence in the test region and time, with such relationship being dependent upon the rate of thermaldiffusion of the total fluorescent labeled reference ligand in the fluid; i.e., both bound and free fluorescent labeled reference ligand. As a result of competition between the fluorescent labeled reference ligand and the ligand for the limited binder sites, an increase in the quantity of ligand in the fluid results in a decrease in the amount of fluorescent labeled reference ligand bound to the binder, which increases the rate of diffusion of total fluorescent labeled reference ligand in the sample, which is detected as an increase in the rate of recovery of fluorescence in the test region.

Thus, in accordance with the present invention, an assay for ligand can be developed by placing in the sample holder a fluid which contains a fixed quantity of binder, a fixed quantity of fluorescent labeled reference ligand, and a known quantity of ligand. The test region is initially subjected to a bleach pulse for a fixed period of time, followed by probe pulses for a fixed duration at fixed intervals, with the fluorescence in the test area at such probe times, being detected by photomultiplier tube 14. The computer 16 then provides a read out of the relationship of the recovery of fluorescence in the test region and time. The procedure is repeated with various known quantities of ligand, whereby there is provided information as to the relationship between recovery of fluorescence and time for each of such known quantities of ligand. Such information can then be provided in a plot, often referred to as a standard curve, with such relationship being conveniently plotted as the recovery of fluorescence achieved at a specific time against the sample ligand concentration or the time required to achieve a specific fluorescence recovery against the sample ligand concentration.

The quantity of ligand present in a serum sample, for example, may then be determined by contacting the serum sample, which is appropriately diluted to greatly reduce any viscosity effects on thermal diffusion, with the fixed quantity of fluorescent labeled reference ligand and the fixed quantity of binder, followed by bleaching for the fixed period of time and probe pulses at the fixed intervals and fixed pulse duration. The recovery of fluorescence after a specific time period, or the time required to achieve a specific recovery of fluorescence is then detected, and compared with the standard curve in order to determine the quantity of ligand present in the serum sample.

Although the procedure has been described with respect to an embodiment which employs a fluorescent labeled reference ligand and unlabeled binder, it is to be understood that such procedure is also applicable to the hereinabove described other embodiments wherein, for example, an assay is effected with use of only a fluorescent labeled binder, or wherein an assay is effected with a fluorescent labeled binder, and a reference ligand which has been modified to move in the fluid at a rate different than the ligand.

It is also to be understood that although the procedure has been described with respect to the use of probe pulses subsequent to photobleaching at predetermined time intervals, the procedure could also be effected with a single non-bleaching pulse, subsequent to photobleaching, which is maintained over a predetermined period of time; i.e., the quantity of light emitted from the test region would be constantly monitored over the pulse period, which would provide a read out of the recovery of fluorescence over such time. It is to be understood, however, that the use of several probe pulses at predetermined intervals is preferred in that the accuracy of the assay is increased.

It is further to be understood that the hereinabove described test system could also be employed in accordance with the hereinabove described embodiment wherein the test region is subjected to photobleaching over a period of time with the test apparatus providing a read out of the relationship of the decrease of fluorescence in the test region and time. Such photobleaching over such time period could be effected by a single photobleaching pulse or by employing a plurality of photobleaching pulses at a predetermined time frequency.

Although the test procedure has been described with respect to the use of a single light beam there could be more than one such light beam. Moreover, although the procedure has been described with respect to a single test region in the fluid, it is to be understood that the procedure could be effected with a plurality of test regions in such fluid. Thus, for example, a sample could be covered with a grid and the entire sample subjected to bleaching and probe pulses, as hereinabove described, with the grid functioning to block the light from reaching portions of the sample thereby providing a plurality of test regions in the sample; e.g., about 50% of the sample can be exposed to radiation and about 50% of the sample protected from radiation.

As another modification, bleaching and monitoring of fluorescence could be effected in different regions. For example, parallel adjacent light beams could be employed for effecting bleaching and probing. In such a case, the probe light pulses would measure a decrease in fluorescence in the probe region which results from movement of bleached material from the region subjected to bleaching into the probe region.

As a further modification, the region of the sample subjected to bleaching radiation can be of a size different than the region of the sample subjected to probing radiation. For example, by the use of appropriate optics, the laser beam for bleaching can have a diameter (D) greater than the probe laser beam diameter (d), which would increase recovery time in that the labeled material must move a greater distance (D-d)/2 in order to be subjected to the probe light pulse. The greater the distance (D-d), the better the discrimination between slow and fast movement, with there being practical limitations on such value (power of laser, heating effects, etc.).

Although the hereinabove described embodiment involves the use of liquid sample in a sample holder, such as a cuvette, it is to be understood that the assay could also be effected in a solid medium, such as a gel. For example, a gel, such as polyacrylamide gel or agar, can be provided with a narrow sample well; e.g., 100 microns diameter, and an appropriate sample placed therein, with a portion of the sample moving into the gel. Bleaching and probe pulses can be employed as hereinabove described by use of a laser beam focussed to pass through the sample well, with material moving from the gel back into the well. Alternatively, the laser beam can be focussed on a region of the gel instead of the sample well with the assay being effected by the procedures hereinabove described except that the various materials move in a gel instead of a liquid. As should be apparent, the solid or gel employed as the test fluid in such embodiments must be one in which at least one of the labeled materials can move, and in the case where probing and bleaching is effected in a region of the gel, the gel must be capable of transmitting light so as to effect the bleaching and probing.

It is also to be understood that the embodiment can be modified by the application of an appropriate force field, as hereinabove described or by supporting one or more substances on a solid support.

The above modifications and others should be apparent to those skilled in the art from the teachings herein.

As should be apparent, the hereinabove described test procedure employing a fluorescent labeled material, basically involves measuring the change in the quantity of fluorescence in a fixed region which results from binding of ligand and binder. Such change in light in the test region is caused by the change in movement in the test region resulting from such binding. The assay can be effected very rapidly in that the change in movement can be detected over very short distances; for example, in the order of 1 to 500 microns. This is accomplished by focussing the light beam on one or more narrow regions.

The invention will be further described with respect to the following examples; however, the scope of the invention is not to be limited thereby:

EXAMPLE I

The equipment for effecting the assay is as shown in FIG. 1 of the drawing, using the following specific components:

Laser—Model 162 10 milliwatt Argon Ion Laser, Spectra Physics, Mountain View, Cal.

Shutter—Uniblitz Model 26L2A14X5, Vincent Associates, Rochester, N.Y.

Shutter Drive Control—Uniblitz Model SD122B, Vincent Associates, Rochester, N.Y.

Photomultiplier Tube—Hamamatsu IP21

Photometer—Pacific Photometric Model 110 Laboratory Photometer

Signal Conditioner—Homemade circuit to convert peak height of pulse and send it out as 5 microsecond pulse.

Analog Digital Converter (ADC)—Nuclear Data 575 ADC

Computer—Model PDP11, Digital Equipment
Terminal—Tektronix Model 4010-1
Shutter Timing Circuit—An Intel #8748 microprocessor controls an adjustable triggering and timing circuit.
Lens—69 mm focal length double convex lens
Cells—1 cm² quartz or borosilicate glass polystyrene microcell—Elkay products
Filter—525nm band pass filter Preparation of Fluorescent labeled Insulin (Fluorescent Labeled reference ligand)

Fluorescein isothiocyanate (FITC) (1 mg; Sigma Chemical Co.) was added with stirring to a suspension of 100 mg. bovine insulin in 30 ml. phosphate-buffered saline (PBS; pH 7.4). The suspension was cooled to 4° C. and the reaction proceeded for 16 hr. After centrifugation, the supernatent was chromatographed on Sephadex G-25 and eluted with PBS. Unreacted FITC remained on the column, and the fluorescent eluant was collected. Upon cooling, a precipitate formed, but the supernatant showed a fluorescence intensity comparable to $10^{-6}$ M fluorescein. This stock solution was then used for immunochemical reaction.

Competitive Binding Assay

Solution of 0.2 ml. of 1:250 dilution of stock FITC-insulin (labeled reference ligand) and 0.2 ml. of the appropriate unlabeled insulin dilutions (ligand) were mixed. An aliquot of guinea pig antibovine insulin (binder) (Cappel Laboratories) was added to each sample, and the solutions were vortexed and then incubated for 2-4 hr. at 6° C. Ten minutes prior to measurement, each sample was allowed to come to room temperature.

Fluorescence was measured in a 1 cm² quartz cuvette with excitation at 488 nm from an argon ion laser. A band pass filter allowed passage of emission wavelengths only greater than 525 nm. Recovery percentages from photobleaching (0.13 sec. pulse) were measured at delay times of 0.50, 1.00, and 2.00 sec.

Figure 2:
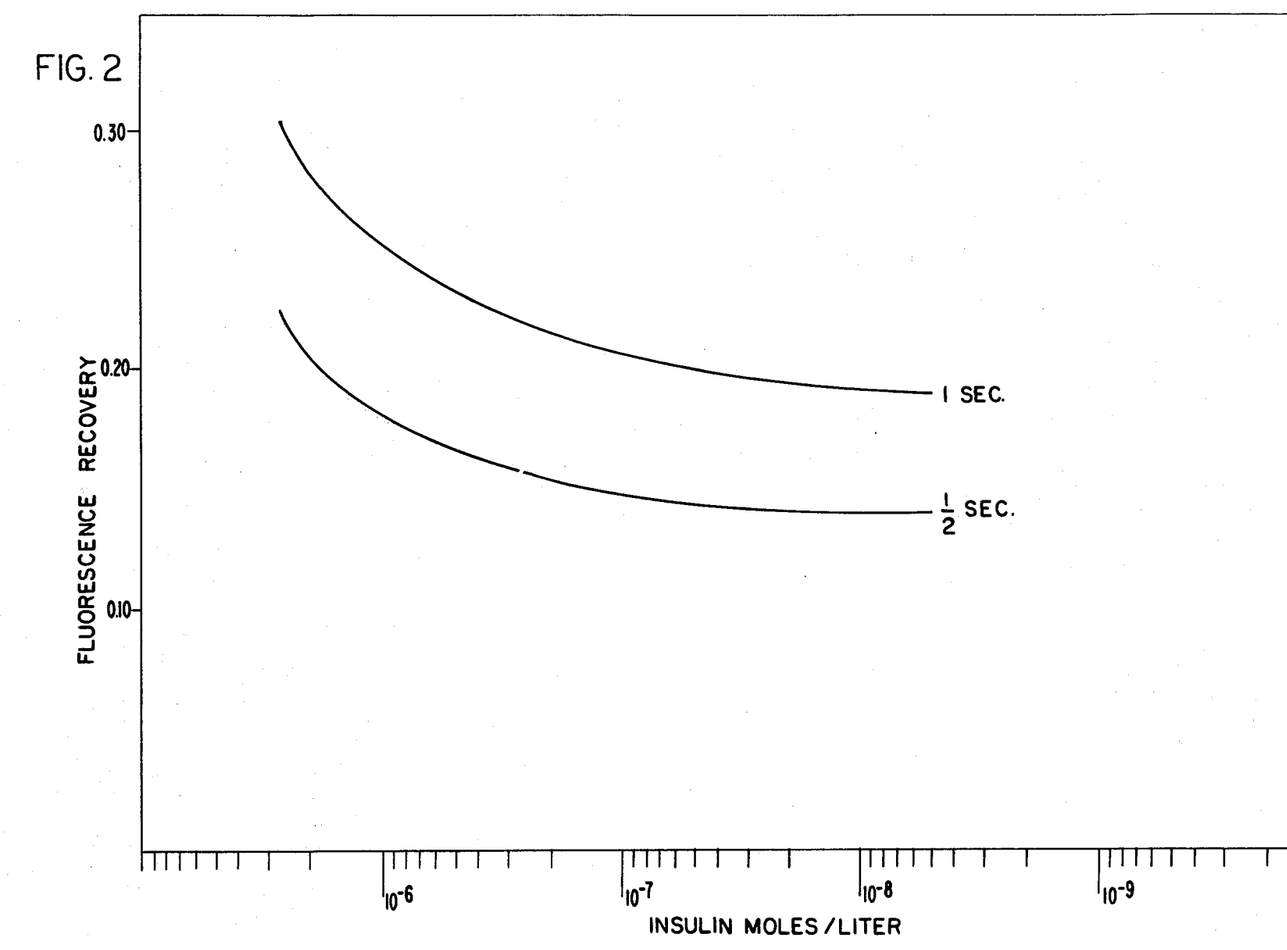
FIGS. 2 and 3 are graphs of fluorescence recovery at specific times versus the log of insulin concentration.
Figure 3:
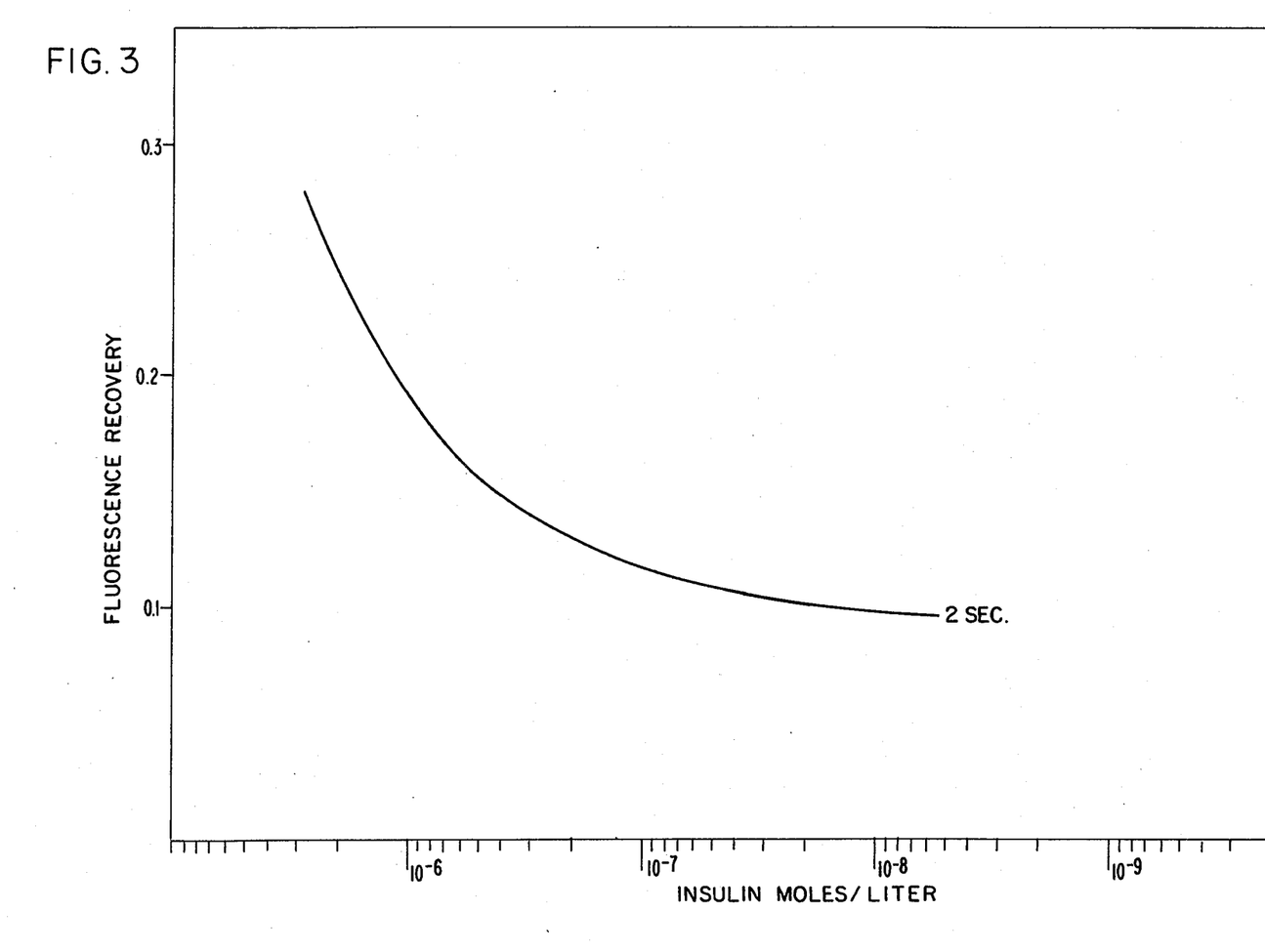

The results are tabulated in the following table and a standard curves of percentage of fluorescence recovery at specific times vs. the log of insulin (ligand) concentration are plotted in FIGS. 2 & 3. Any of such standard curves can be employed to measure unknown insulin concentrations in a sample.

| (Insulin) Moles/l | Percentage of Fluorescence Recovery at specific times | | |
|---|---|---|---|
| | 0.50 sec. | 1.00 sec. | 2.00 sec. |
| $2.7 \times 10^{-6}$ | 0.231 | 0.313 | 0.482 |
| $2.0 \times 10^{-6}$ | 0.183 | 0.281 | 0.414 |
| $1.0 \times 10^{-6}$ | 0.172 | 0.277 | 0.392 |
| $8 \times 10^{-7}$ | 0.170 | 0.263 | 0.388 |
| $6 \times 10^{-7}$ | 0.179 | 0.244 | 0.367 |
| $4 \times 10^{-7}$ | 0.160 | 0.212 | 0.322 |
| $2 \times 10^{-7}$ | 0.148 | 0.230 | 0.360 |
| $1 \times 10^{-7}$ | 0.134 | 0.195 | 0.351 |
| $5 \times 10^{-8}$ | 0.148 | 0.198 | 0.301 |
| $5 \times 10^{-9}$ | 0.137 | 0.187 | 0.301 |

EXAMPLE II

The assay of the present invention is illustrated by the case wherein there is mixed an antigen A (ligand), the fluoroscein labeled antigen FA (reference ligand) and antibody Ab (binder), with the immunochemical reaction being represented as follows:

$$Ab + FA \rightleftharpoons AbFA \quad (1)$$

$$Ab + A \rightleftharpoons AbA \quad (2)$$

In this case, it is assumed that the thermal diffusion constant of the antibody molecule is one or two orders of magntiude less than the antigen because of its larger size and that return of fluorescent molecules to the photobleached region is by thermal diffusive motion. At equilibrium the resulting solution will contain an equilibrium concentration of AbA, AbFA, A and FA. The fraction of the molecules FA that are "free", and the fraction of the molecules FA that are bound to antibody (AbFA) clearly depends on the relative amounts of Ab, A and FA according to elementary chemical equilibrium theory. Thus the amount of A in the unknown solution is related quantitatively to the concentrations of FA and Ab in the initial mixture, and under specified conditions a determination of the ratio of these concentrations suffices for a determination of A in the unknown. Alternatively, the measurement of any property of the system quantitatively and monotonically related to the ratio of these concentrations can be used as the basis of an assay for A in the unknown.

Let $f_{FA}(t)$ be the normalized photobleach recovery function for FA, and let $f_{AbFA}(t)$ be the normalized photobleach recovery function for AbFA. For example, $$f(t) = (L - L_{min})/(L_{max} - L_{min}) \quad (3)$$

wherein L is the fluoresence intensity at time t; $L_{max}$ is the fluoresence intensity immediately prior to photobleach; and $L_{min}$ is the fluorescence intensity immediately after photobleach.

Now, if the average lifetime of the "bound" and "free" molecules are long as compared to photobleach and recovery times, the recovery curve in the assay mixture is:

$$f(t) = Xf_{FA}(t) + (1 - X)f_{AbFA}(t) \quad (4)$$

where X = fraction of the fluorescene due to the free molecules, before bleaching.

In accordance with equation (4), it is possible to determine the value of X by measuring the fractional recovery at a specified time; e.g., f(1 sec), and from previously measured values of $f_{FA}$ (1 sec); i.e., fluorescene recovery of a sample containing only "free" labeled antigen, and $f_{AbFA}$ (1 sec); i.e., fluorescene recovery of a sample containing only "bound" labeled antigen.

Figure 4:
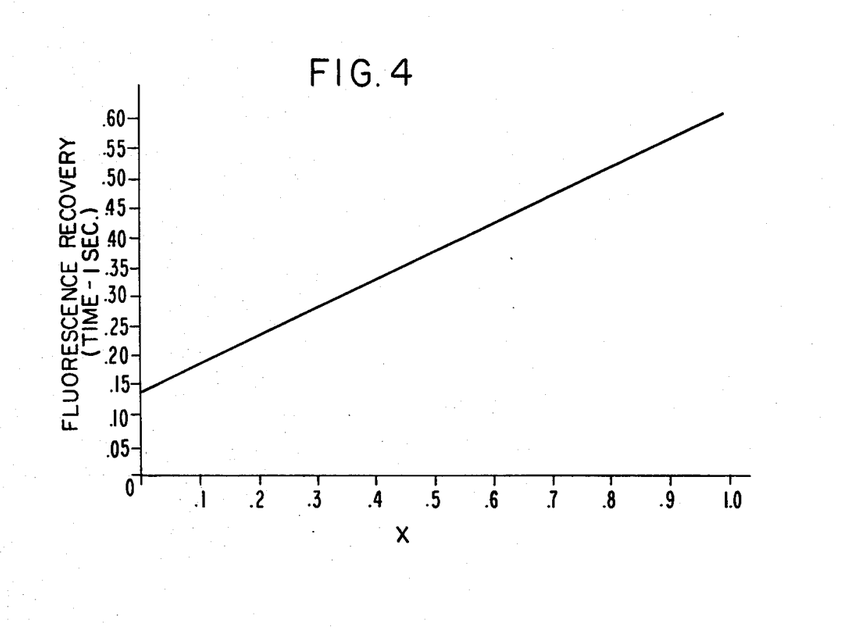
FIG. 4 is a graph of fluorescence recovery at a specific time for mixture of fluorescein and fluorescein labeled antibody.

The validity of the linear superposition of recovery curves (equation 4) was demonstrated experimentally by mixing various proportions of two solutions, one containing $10^{-8}$ molar sodium fluorescein in phosphate buffer to represent FA and the other a solution of fluorescein labeled antibodies (FITC-IgG) in phosphate buffer to represent AbFA (the second solution had twice the fluorescence intensity of the first). Nine different mixtures of these solutions were prepared and the photobleach recovery curves determined (488 nm laser source, 60 mm focusing lens, bleach pulse = 140 ms, probe pulse = 1.4 ms. Percent recovery at t = 1 sec was measured). The results are shown in FIG. 4. At a given fractional recovery f (1 sec), one can determine X, and X can be related quantitatively to the composition of the solution. Likewise a plot of the time required for 50% recovery, illustrated in FIG. 5 forms the basis of a quantitative assay.

Figure 5:
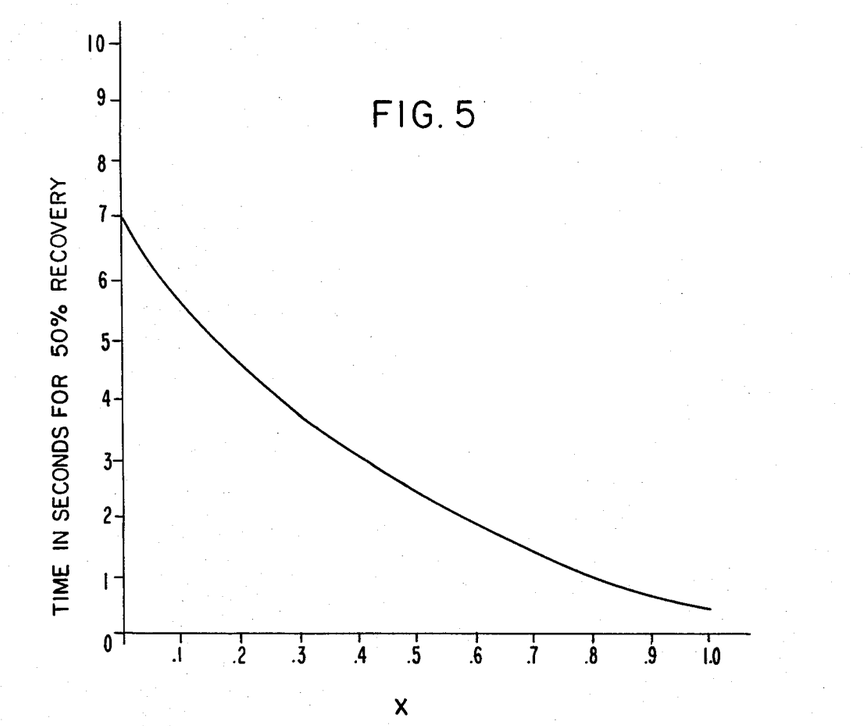
FIG. 5 is a graph of time to achieve 50% fluorescence recovery for mixtures of fluorescein and fluorescein labeled antibody.

A competitive binding assay is then carried out as follows. A solution containing an unknown concentration of A is mixed with solutions containing appropriate concentrations of FA and Ab directed against A (and FA). Equation (4) still applies and X can be determined from a plot such as the one illustrated in FIGS. 4 or 5. In general, an empirical assay curve relating X and the concentration of A must be determined, so that the concentration of A in the unknown can be related to the observed value of X. In the simple case where X is equal to the fraction of the FA molecules that are free, and $1-X$ is the fraction of FA molecules that are bound as AbFA then the concentration A of antigen in the solution is $$A = F_b/(1-X) - c_0 - K/X$$

where $F_b$ = total antibody receptor site concentration as measured by the maximum concentration of labeled antigen FA that can be bound, and K = the dissociation constant for FA (the labeled antigen), and $c_O$ is the total concentration of labeled antigen, FA.

Figure 6:
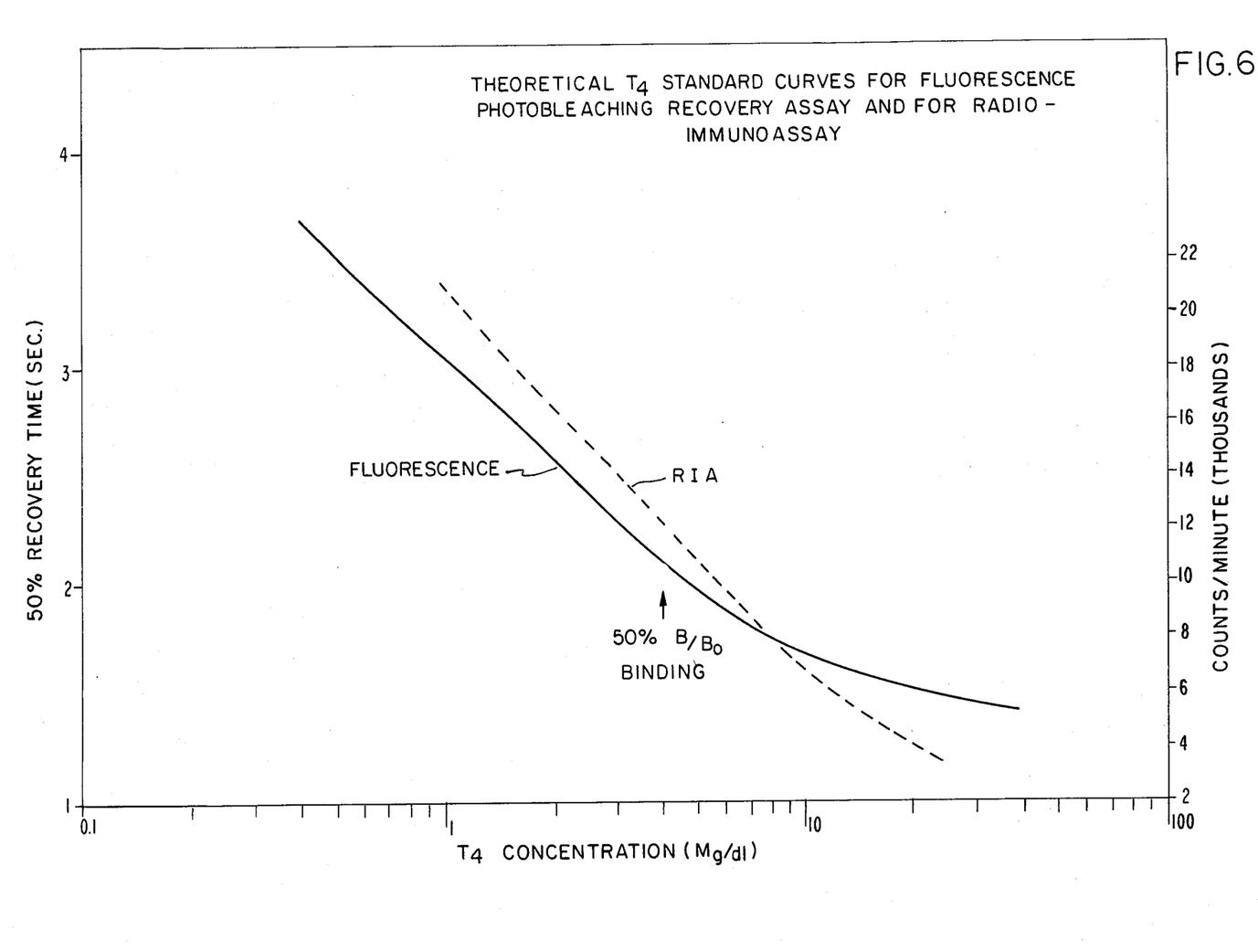
FIG. 6 is a theoretical standard curve for a photobleach recovery assay for $T_4$, compared with a $T_4$ radioimmunoassay standard curve.

FIG. 6 illustrates the results of a theoretical standard curve for photobleach recovery assay for $T_4$, as compared with a typical standard curve for R1A. (For the R1A curve, see Ref. booklet, $T_4$ Solid Phase Radioimmunoassay Kit [$I^{125}$], Becton, Dickinson and Company (March, 1978)). For the theoretical curve the following assumptions were made: (a) $K = 10^{-10}$ liter/mole, $c_O = 5 \times 10^{-8}$ mole/liter, $F_b = 2.5 \times 10^{-8}$ mole/liter, the thermal diffusion constant for bound $T_4$ to be $4 \times 10^{-7}$ cm$^2$/sec, and that for free $T_4$ to be $4 \times 10^{-6}$ cm$^2$/sec, that the fluorescence properties of $FT_4$ and $AbFT_4$ are the same, a laser beam radius of $40\mu$, and a bleaching parameter corresponding to 70% bleaching.

Numerous modifications and variations of the present invention are possible in light of the above teachings and, therefore, within the scope of the appended claims the invention may be practiced otherwise than as particularly described.

I claim:

1. An assay for a ligand, comprising:
contacting in a fluid a ligand with one of (a) labeled binder or (b) binder and labeled reference ligand; and determining the rate of movement of labeled material in at least one region of the fluid to determine the presence of ligand.

2. The process of claim 1 wherein the movement is determined by measuring the relationship of the amount of labeled material in the at least one region and time.

3. The assay of claim 2 wherein the label is a fluorescent label.

4. The process of claim 3 wherein the relationship of the increase of fluorescent material in the at least one region and time is determined.

5. The assay of claim 3 wherein the relationship of decrease in fluorescent material in the region and time is measured.

6. The assay of claim 3 wherein the contacting is effected with binder and fluorescent labeled reference ligand.

7. The assay of claim 3 wherein the fluid is a liquid.

8. The assay of claim 3 wherein the relationship of the amount of fluorescent labeled material in the region and time is measured by detecting the change in the amount of light emitted from fluorescent material in the at least one region.

9. The assay of claim 3 wherein the contacting is effected with fluorescent labeled binder.

10. The assay of claim 9 wherein the contacting is further effected in the presence of a reference ligand modified to move in the fluid at a rate different than the ligand.

11. The process of claim 3 wherein the movement in the at least one region is effected in the presence of at least one applied force field.

12. The assay of claim 11 wherein the force field is a magnetic force field.

13. The process of claim 11 wherein the at least one applied force field is a gravitational force field.

14. The assay of claim 11 wherein the at least one applied force field is an electrical force field.

15. An assay for a ligand, comprising:
contacting in a fluid a ligand with one of (a) fluorescent labeled binder or (b) binder and fluorescent labeled reference ligand;
bleaching at least one region of the fluid; and
measuring the relationship of change of fluorescence and time in at least one region of the fluid.

16. The assay of claim 15 wherein the assay is effected with an applied electrical force field during at least one of the bleaching and measuring.

17. The assay of claim 16 wherein the ligand is contacted with fluorescent labeled binder and reference ligand, said reference ligand having a charge whereby the reference ligand has a rate of movement in the applied electrical force field different than the ligand.

18. The assay of claim 16 wherein the ligand is contacted with binder and fluorescent labeled reference ligand, with the binder having a charge whereby the labeled reference ligand bound to the binder has a rate of movement in the applied electrical force field which is different than the unbound labeled reference ligand and the electrical force field is applied during at least one of said bleaching and measuring.

19. The assay of claim 15 wherein the bleaching is effected by photobleaching.

20. The assay of claim 19 wherein the relationship of increase of fluorescence and time is measured.

21. The assay of claim 19 wherein the ligand is contacted with fluorescent labeled binder having a charge whereby the fluorescent labeled binder has a rate of movement in the applied electrical force field different than the ligand.

22. The assay of claim 19 wherein the ligand is contacted wit labeled binder supported on a solid support.

23. The assay of claim 19 wherein the ligand is contacted with binder supported on a solid support and labeled reference ligand.

24. The assay of claim 19 wherein the ligand is contacted with labeled binder and reference ligand supported on a solid support.

25. The assay of claim 19 wherein the ligand is contacted with fluorescent labeled binder and reference ligand modified to move in the fluid at a rate different than the ligand.

26. The assay of claim 19 wherein the fluid is a liquid.

27. The assay of claim 19 wherein measuring is effected in a region within the bleaching region.

28. The assay of claim 27 wherein the measuring is effected in a region having a cross-sectional area smaller than the bleaching region.

29. The assay of claim 27 wherein measuring and bleaching are effected in the same region.

30. The assay of claim 19 wherein the relationship of decrease of fluorescence and time is measured.

31. The assay of claim 30 wherein the bleaching and measuring are effected in adjacent regions.

32. The assay of claim 30 wherein the bleaching and measuring are effected in the same region.

33. The assay of claim 19 wherein the assay is effected with an applied magnetic force field during at least one of the bleaching and measuring.

34. The assay of claim 33 wherein the ligand is contacted with fluorescent labeled binder supported on a magnetic material whereby binding of ligand to the binder changes movement of the labeled binder in the applied magnetic field.

35. The assay of claim 33 wherein the ligand is contacted with binder supported on magnetic material and labeled reference ligand.

36. The assay of claim 33 wherein the ligand is contacted with labeled binder and reference ligand supported on magnetic material.

37. The assay of claim 19 wherein the ligand is contacted with binder and fluorescent labeled reference ligand.

38. The assay of claim 37 wherein the bleaching is effected with a focussed beam of light in a narrow region.

39. The assay of claim 38 wherein the relationship of the increase of fluorescence and time is measured within the at least one region which is bleached.

40. The assay of claim 38 wherein the relationship of the decrease of fluorescence and time is measured during bleaching in said at least one region.

41. The assay of claim 19 wherein the ligand is contacted with fluorescent labeled binder.

42. The assay of claim 41 wherein the bleaching is effected with a focussed beam of light in a narrow region.

43. The assay of claim 42 wherein the relationship of the increase of fluorescence and time is measured within the at least one region which is bleached.

44. The assay of claim 42 wherein the relationship of the decrease of fluorescence and time is measured during bleaching in said at least one region.

45. An assay for a ligand, comprising:

contacting in a fluid a ligand with one of (a) a binder and a fluorescent labeled reference ligand or (b) fluorescent labeled binder;

subjecting at least one region of the fluid to a photobleaching light pulse; and subsequently subjecting at least a portion of said at least one region to time spaced non-bleaching probe light pulses and detecting fluorescent light emission during said probe light pulses to thereby measure the relationship of recovery of fluorescence and time within said at least one region.

46. The assay of claim 45 wherein the assay is a quantitative assay for the ligand, the ligand is contacted with binder and fluorescent labeled reference ligand, the time to achieve a predetermined fluorescence recovery is measured and the measured time is compared with a standard curve depicting the relationship of ligand quantity and time to achieve the predetermined fluorescence recovery.

47. The assay of claim 45 wherein the assay is a quantitative assay for the ligand, the ligand is contacted with binder and fluorescent labeled reference ligand, the fluorescence recovery in a predetermined time is measured and the measured fluorescence recovery is compared with a standard curve depicting the relationship of ligand quantity and fluorescence recovery achieved in said predetermined time.

48. The assay of claim 45 wherein the fluid is a liquid.

49. The assay of claim 48 wherein the ligand is contacted with binder and fluorescent labeled reference ligand.

50. The assay of claim 49 wherein the time to achieve a predetermined fluorescence recovery is measured.

51. The assay of claim 49 wherein the recovery of fluorescence after a predetermined time is measured.

52. The assay of claim 49 wherein the photobleaching light pulse and probe light pulse are effected with a focussed laser beam.

53. The assay of claim 48 wherein the ligand is contacted with fluorescent labeled binder.

54. The assay of claim 53 wherein the photobleaching light pulse and probe light pulse are effected with a focussed laser beam.

55. The assay of claim 53 wherein the recovery of fluorescence after a predetermined time is measured.

56. The assay of claim 53 wherein the time to achieve a predetermined fluorescence recovery is measured.

* * * * *